United States Patent [19]

Bouillon et al.

[11] 4,363,796

[45] Dec. 14, 1982

[54] COSMETIC COMPOSITIONS FOR HARDENING SOFT BRITTLE NAILS

[75] Inventors: Claude Bouillon, Eaubonne; Jean Boulogne, L'Hay-les-Roses; Michel Guillon, Bourg-la-Reine; Christian Zaffran, Elancourt; Constantin Koulbanis, Paris, all of France

[73] Assignee: Societe Anonyme dite: L'Oreal, Paris, France

[21] Appl. No.: 967,256

[22] Filed: Dec. 5, 1978

[30] Foreign Application Priority Data

Dec. 16, 1977 [FR] France ............... 77 37991

[51] Int. Cl.$^3$ ............... A61K 7/04
[52] U.S. Cl. ............... 424/61
[58] Field of Search ............... 424/61

[56] References Cited

U.S. PATENT DOCUMENTS

| 2,887,116 | 5/1959 | Wooding | 424/61 X |
| 3,034,966 | 5/1962 | Williams | 424/61 |
| 3,349,000 | 10/1967 | Joos | 424/61 |
| 3,483,289 | 12/1969 | Michaelson et al. | 424/61 |
| 3,510,554 | 5/1970 | Balsiger | 424/61 |
| 3,725,525 | 4/1973 | Joos | 424/61 |
| 3,907,580 | 9/1975 | van Ham | 424/61 |
| 3,928,561 | 12/1975 | Baldwin | 424/61 |
| 4,032,464 | 6/1977 | Mausner | 424/61 |

FOREIGN PATENT DOCUMENTS

| 928728 | 6/1955 | Fed. Rep. of Germany | 424/61 |
| 1813842 | 7/1969 | Fed. Rep. of Germany | 424/61 |
| 1201005 | 7/1959 | France | 424/61 |
| 1521072 | 3/1968 | France | 424/61 |
| 1193514 | 5/1970 | United Kingdom | 424/61 |
| 1255640 | 12/1971 | United Kingdom | 424/61 |

OTHER PUBLICATIONS

Martindale, The Extra Pharmacopoeia, vol. I, 24th Edition, 1958, pp. 306 & 307.

Primary Examiner—Dale R. Ore
Attorney, Agent, or Firm—Cushman, Darby & Cushman

[57] ABSTRACT

Cosmetic composition for hardening nails is formed from trimethylolmelamine or tris-(hydroxymethylamino)-2, 4, 6 s triazine; at least one non-cationic cosmetic resin and/or at least one cationic resin; a plasticizer and an acid.

16 Claims, No Drawings

COSMETIC COMPOSITIONS FOR HARDENING SOFT BRITTLE NAILS

The present invention is directed to a new cosmetic composition for reinforcing nails, particularly brittle nails or soft nails.

The compositions according to the invention are particularly useful for application to fragile nails which have a tendency to split or to bend and fracture.

Such compositions called, "nail hardeners", have already been proposed. For instance, liquid compositions consisting of an aqueous solution of stearyl trimethylammonium chloride (3%), the nonyl phenol ether of polyoxyethylene (1.5%), and triethanolamine stearate (0.5%) have been proposed as "nail hardeners".

However, it has been established that said compositions do not provide appreciable reinforcement of the nails, and moreover, it is difficult to apply to the treated nail an uncolored or colored nail varnish or polish, which has a good adhesion to the nail.

Nail hardening compositions in which the principal active component is formol (formaldehyde), in a concentration generally ranging from 4 to 15% have also been proposed. But, these compositions present certain risks and disadvantages, on account of the possible reaction of the formol with skin proteins.

Indeed, it has been established that repeated applications of such compositions induce skin reactions and the phenomenon of tissue irritation.

In order to remedy these inconveniences and disadvantages and with the object of obtaining a composition allowing application of a nail cosmetic, in the form of a colored varnish thereto, a new composition for hardening fragile and split nails has been developed. This composition contains, as a principal active component either trimethylomelamine or tris-(hydroxymethylamino)-2,4,6 s-triazine.

Through regular application of these cosmetic compositions, it has been established that the trimethylolmelamine has a great affinity for the nails and allows hardening of the nails, to obviate splitting of the nails.

Moreover, the compositions based on this compound are substantially free of free formol, which avoids skin reactions, and notably skin irritations.

Moreover, the compositions according to the invention form a uniform film, which, after drying, permit the application thereto of an uncolored or colored nail varnish.

The present invention has for an object, a new industrial product, a cosmetic composition for nail reinforcement, notably for hardening the nails to obviate their splitting and cracking. The composition of the invention comprises an aqueous, alcoholic or hydroalcoholic solution of
 (i) trimethylolmelamine,
 (ii) at least one non-cationic cosmetic resin and/or at least one cationic resin,
 (iii) at least one plasticizer agent, and
 (iv) an orangic or mineral acid.

In the compositions according to the invention, the amount of trimethylolmelamine is from 3 to 10%, and preferably between 4 and 6% by weight, based on the total weight of the composition.

The cosmetic resins utilized in the compositions of the invention are conventional resins which are preferably soluble in water. Among the non-cationic resins, such synthetic resins include, polyvinyl alcohols, polyvinylpyrrolidones, copolymers of vinylpyrrolidone and vinyl acetate (70/30 to 30/70), copolymers of vinyl acetate and unsaturated carboxylic acids, and in particular the copolymers of vinyl acetate and crotonic acid; these copolymers are in salt form, as a result of treatment with a mineral or organic base, including hydroxylated amines, such as 2-amino 2-methyl 1-propanol, 2-amino 2-methyl 1,3-propanediol and triisopropanolamine; other copolymers include those of an alkylvinylether and maleic anhydride, which are in the salt form by treatment with said organic or mineral base and/or are semi-esterified with an aliphatic alcohol having 1–5 carbon atoms.

Non-cationic resins which can be used in the compositions of the invention include natural resins, such as gum arabic or cellulose derivatives such as hydroxyethylcellulose.

Cationic resins which can be used in the compositions of the invention can be used alone or in admixture with a non-cationic resin; these include the resins described in French Brevet Nos. 2.252.840 and 76.15948; resins described in French Brevet No. 1.583.363, assigned to Sandoz and notably resins sold under the trade name "CARTARETINE F4"; the resins described in French Brevet No. 71.03018 to General Anilin and Film Corporation and notably the resins sold under the trade name "GAFQUAT 755"; and cationic cellulose derivatives described in French Brevet No. 1.492.597 to Union Carbide and notably the cellulosic derivatives sold under the commercial denomination of "JR 400". Said French Brevets 2.252.840; 76.15948; 1.583.363; 71.03018 and 1.492.597 are incorporated by reference herein.

The amount of the cosmetic resin in the compositions of the invention depends on the nature of the resin employed.

The amount of non-cationic resins in the compositions of the invention range of from 0.1 to 5% by weight, and preferably from 1 to 2.5% by weight of the composition.

If a cationic resin is employed, its amount ranges preferably between 0.1 and 0.5% by weight of the composition.

When a mixture of a non-cationic and a cationic resin is employed in compositions of the invention, the cationic resin is present in an amount up to 0.5% by weight of the composition, and the total concentration of the combined resins in the compositions ranges between 0.1 and 5% by weight of the total composition.

The plasticizer agent which allows for the plasticizing and hardening of the film of the composition on the nails can be a lanolin which is polyoxyethylenated with 5 to 20 moles of ethylene oxide or with polyglycols such as polyethyleneglycols having molecular weights ranging from 200 to 1,000.

According to the invention, the plasticizer agent is generally present in an amount ranging from 2 to 6% by weight of the total weight of the composition, and preferably from 2.5 to 4.5% by weight.

The mineral or organic acid component of the composition of the invention is utilized to maximize the solubility of the trimethylolmelamine. Preferably hydrochloric acid is used, as the mineral acid but it is also possible to employ phosphoric acid, as well as organic acids such as malic acid, tartaric acid, and citric acid.

When the compositions of the invention are in the form of aqueous or hydroalcoholic (aqueous-alcoholic) solutions, the pH thereof can vary from 1.5 to 3.

The alcohol, in the alcoholic or the hydroalcoholic solution of the compositions of the invention, is generally ethanol but can also be isopropanol.

The alcohol concentration in the hydroalcoholic compositions can vary from 2 to 90% and preferably from 8 to 20% by weight of the total composition.

The compositions of the invention can also contain other ingredients, such as wetting agents, vitamins, xanthic bases, dyes and colorants, perfumes, proteins or solar filters.

The wetting agents allow for improved contact, and thus improved adhesion to the nail by increasing wetting of the surface of the nail. Wetting agents which can be used in the compositions of the invention can include the esters of sorbitan polyoxyethylenated with a fatty acid such as lauric acid, oleic acid, palmitic acid, or stearic acid, fluorinated non-ionic surface active agents, such as those known under the commercial denominations of "MONFLOR" sold by Imperial Chemical Industries or polyoxyethylenes of alkylphenols, such as isooctyl phenol polyoxyethylenated with 10 moles of ethylene oxide sold by Rohm and Haas under the commercial denomination of "TRITON X 100".

According to the invention the concentration of the wetting agent can range from 0.1 to 0.5%, and preferably from 0.2 to 0.3% by weight of the total weight of the composition.

The vitamins which can be introduced into the compositions according to the invention can include vitamin A, vitamin B, vitamin D, or vitamin E. These vitamins can be present in the composition in an amount ranging from 0.01 to 0.2%; preferably the composition contains 0.1% of a vitamin complex sold by Merck sold under the commercial denomination of "AD3E" containing by ml: 180.000 iU of vitamin A, 130.000 iU of vitamin $D_3$ and 6 mg of vitamin E (in the form of the acetate).

Among the xanthic bases which can be used in the compositions of the invention, are theophylline and caffeine. The xanthic bases are present in the compositions of the invention in an amount from 0.05 to 0.5% by weight of the composition, preferably from 0.2 to 0.3% by weight of the total composition.

The present application has for an object a process of reinforcing nails to harden the nails and to avoid their splitting; the process consists in applying to the surface of the nail, in an ordinary manner, a composition such as defined above with a brush.

In order to maximize the effect of the compositions of the invention, daily application of the compositions of the invention is recommended, preferably in the evening to allow prolonged action during the night.

After the composition of the invention has dried on the nail(s), uncolored or colored nail varnishes or polishes can be applied in a manner to avoid elimination of the product by washing or by rubbing.

It has been established that excellent adhesion of film or nail varnishes can be realized on the pre-applied composition of the invention.

The following examples do not limit, but rather illustrate compositions of the invention which is to be interpreted in accordance with the scope of the appended claims.

EXAMPLES OF THE COMPOSITIONS

EXAMPLE 1

A composition of the invention for reinforcing the nails is prepared by mixing the following ingredients:

| | |
|---|---|
| Trimethylolmelamine | 4 g |
| Polyvinylpyrrolidone K 30 (M.W. = 40,000) | 3 g |
| Ethanol | 20 g |
| Lanolin polyoxyethylenated with 5 to 20 moles of ethylene oxide | 3 g |
| Hydrochloric acid 5N q.s.p. pH 3 | |
| Demineralized water q.s.p. | 100 g |

By daily application of this composition onto fragile nails having a tendency to crack, hardening of the nails, which no longer have a tendency to split, results.

EXAMPLE 2

A composition for reinforcing nails, in accordance with the invention, is prepared by mixing the following ingredients:

| | |
|---|---|
| Trimethylolmelamine | 5 g |
| A copolymer of vinylpyrrolidone/vinyl acetate (70/30) | 2 g |
| Polyethylene glycol 400 | 4 g |
| Ethanol | 10 g |
| Monolaurate of polyoxyethylenated sorbitan (Tween 20) | 0.2 g |
| Hydrochloric acid q.s.p. pH 3 | |
| Demineralized water q.s.p. | 100 g |

EXAMPLE 3

A composition for reinforcing nails, in accordance with the invention, is prepared by mixing the following ingredients:

| | |
|---|---|
| Trimethylolmelamine | 5 g |
| Polyvinyl alcohol (Rhodoviol 4/125 P) (ester index 120-150) | 2 g |
| Isopropanol | 10 g |
| Theophylline | 0.3 g |
| Cationic polymer, prepared in accordance with Example 1 (which is incorporated by reference herein) of French Brevet No. 2,252,840 | 0.5 g |
| Vitamin "A $D_3$ E" (Merck) | 0.1 g |
| Lanolin polyoxyethylenated with 5 to 20 moles of ethylene oxide | 4 g |
| Phosphoric acid, q.s.p. pH 3 | |
| Demineralized water, q.s.p. | 100 g |

EXAMPLE 4

A composition for reinforcing nails, in accordance with the invention, is prepared by mixing the following ingredients:

| | |
|---|---|
| Trimethylolmelamine | 8 g |
| Gum arabic | 4 g |
| Polyethyleneglycol 600 | 2 g |
| Fluorinated non-ionic surface active agent ("MONFLOR") | 0.3 g |
| Hydrochloric acid, q.s.p. pH 1.5 | |
| Demineralized water, q.s.p. | 100 g |

By daily application of this composition to splitting and fragile nails, hardening of said nails is obtained after several days of application.

EXAMPLE 5

A composition for hardening nails, in accordance with the invention, is formed by mixing the following ingredients:

| | |
|---|---|
| Trimethylolmelamine | 6 g |
| Cationic cellulosic polymer derivative "JR 400" (viscosity of 300–500) | 0.5 g |
| Ethanol | 8 g |
| Polyethyleneglycol 1000 | 5 g |
| Theophylline | 0.1 g |
| Malic acid, q.s.p. pH 3 | |
| Demineralized water, q.s.p. | 100 g |

EXAMPLE 6

A composition for reinforcing nails, in accordance with the invention, was prepared by mixing the following ingredients:

| | |
|---|---|
| Trimethylolmelamine | 5 g |
| Hydroxyethyl cellulose | 2 g |
| Ethanol | 12 g |
| Lanolin polyoxyethylenated with 5 to 20 moles of ethylene oxide | 4 g |
| Caffeine | 0.1 g |
| Polyoxyethylenated isooctyl phenol (Triton X 100) | 0.2 g |
| Tartaric acid, q.s.p. pH 2.8 | |
| Demineralized water, q.s.p. | 100 g |

EXAMPLE 7

A composition of the invention was prepared by mixing the following ingredients:

| | |
|---|---|
| Trimethylolmelamine | 6 g |
| Resin "GAFQUAT 755" | 0.5 g |
| Isopropanol | 10 g |
| Polyoxyethylenated lanolin | 3 g |
| Stearate of polyoxyethylenated sorbitan | 0.2 g |
| Soluble collagen | 0.1 g |
| Citric acid, q.s.p. pH 3 | |
| Demineralized water, q.s.p. | 100 g |

EXAMPLE 8

A composition for reinforcing nails, in accordance with the invention, was prepared by mixing the following ingredients:

| | |
|---|---|
| Trimethylolmelamine | 5 g |
| Polyvinylpyrrolidone K 30 | 3 g |
| Ethanol | 10 g |
| Palmitate of polyoxyethylenated sorbitan | 0.2 g |
| Polyoxyethylenated lanolin | 3.5 g |
| Cationic copolymer prepared in accordance with Example 1 of French Brevet No. 2.252.840 | 0.2 g |
| Hydrochloric acid 5 N, q.s.p. pH 2.5 | |
| Demineralized water, q.s.p. | 100 g |

What is claimed is:

1. A cosmetic composition for reinforcing nails comprising an aqueous, an alcoholic or a hydroalcoholic solution of
   (i) 3 to 10% by weight of trimethylolmelamine;
   (ii) 0.1 to 5% by weight of at least one non-cationic cosmetic resin, one cationic cosmetic resin, or admixtures thereof;
   (iii) at least one plasticizer; and
   (iv) a mineral or organic acid.

2. The composition of claim 1 wherein the trimethylolamine is present in an amount of from 4 to 6% by weight of the total composition.

3. The composition of claim 1 wherein the non-cationic or cationic resin is soluble in water.

4. The composition of claim 1 wherein the cosmetic resin is a non-cationic resin and is present in an amount of from 1 to 2.5% by weight of the total composition.

5. The composition of claim 1 wherein said resin is a cationic resin and is present in an amount ranging from 0.1 to 0.5% by weight of the total composition.

6. The composition of claim 1 wherein said cosmetic resin is a mixture of a non-cationic resin and a cationic resin, the latter being present in a concentration up to 0.5% by weight, the composition containing between 0.1 to 5% by weight of resin.

7. The composition of claim 1 wherein said plasticizer is lanolin polyoxyethylenated with 5 to 20 moles of ethylene oxide or a polyethylene glycol having a molecular weight of from 200 to 1,000.

8. The composition of claim 1 wherein said plasticizer is present in an amount of from 2 to 6% by weight.

9. The composition of claim 1 wherein said acid is hydrochloric acid, phosphoric acid, malic acid, tartaric acid or citric acid.

10. The composition of claim 1 wherein said hydroalcoholic solution contains 2 to 90% by weight of ethanol or of isopropanol.

11. The composition of claim 1 which also includes at least one wetting agent in an amount ranging from 0.1 to 0.5% by weight of the composition.

12. The composition of claim 1 which also includes vitamin A, vitamin B, vitamin D, vitamin E or mixtures thereof.

13. The composition of claim 1 which also includes theophylline or caffine in an amount of from 0.05 to 0.5% by weight of the total composition.

14. The composition of claim 1 which also includes a perfume, a dye, a colorant, a protein or a solar filter.

15. The process of reinforcing nails in order to harden them and to obviate splitting comprising applying to the surface of the nail an effective amount of the composition of claim 1.

16. The process of of claim 15 which includes, after applying and drying said composition, applying a colored or uncolored nail varnish to the dried composition.

* * * * *